United States Patent [19]

Ripple et al.

[11] Patent Number: 4,913,034

[45] Date of Patent: Apr. 3, 1990

[54] AIR HANDLING SYSTEM WITH DEODORIZER INJECTION

[76] Inventors: Joseph E. J. Ripple, 8140 NW. 13th St., Pembroke, Fla. 32503; Daniel E. Kelly, 2727 NW. 167th St., Miami, Fla. 33054

[21] Appl. No.: 293,189

[22] Filed: Jan. 3, 1989

[51] Int. Cl.$^4$ ............................................. B60H 1/32
[52] U.S. Cl. ................................... 98/2.11; 126/113; 239/34; 261/DIG. 17
[58] Field of Search ...................... 62/78, 309; 165/19; 98/30, 2.11, 105, 109; 239/289, 34; 261/104, DIG. 17; 126/113

[56] References Cited

U.S. PATENT DOCUMENTS

| | | | |
|---|---|---|---|
| 3,640,266 | 2/1972 | Ernest | 126/113 |
| 3,776,214 | 12/1973 | Coffman | 126/113 |
| 4,677,902 | 7/1987 | Takemasa | 98/2.11 |
| 4,805,520 | 2/1989 | Freedman | 98/2.11 |

FOREIGN PATENT DOCUMENTS 2556242  6/1985  France ................................ 239/289

Primary Examiner—William E. Wayner
Attorney, Agent, or Firm—Fleit, Jacobson, Cohn, Price, Holman & Stern

[57] ABSTRACT

The air handling duct structure of an automotive vehicle having inlet and outlet ends and liquid heat exchange structure serially disposed within the duct structure intermediate the ends as well as blower structure serially disposed in the duct structure at a location therealong spaced intermediate the inlet end and the heat exchange structure includes liquid injection structure opening into an exposed wall portion of the duct structure at the aforementioned location thereof and is operative, when actuated, to inject a deodorizing liquid (and also possibly a disinfectant liquid) into the interior of the duct structure at the aforementioned location therealong.

4 Claims, 1 Drawing Sheet

AIR HANDLING SYSTEM WITH DEODORIZER INJECTION

BACKGROUND OF THE INVENTION

1. Field of the Invention

This invention relates to an apparatus by which a deodorizing agent is injected into the inlet end of the air handling ducting of an automobile air conditioning and heating system. The deodorizer may be natural, artificial or organic and will be in liquid form. Also, the deodorizer may further incorporate a disinfectant, inasmuch as it has been found that certain undesirable mold and bacteria may build up within an air conditioning system.

2. Description of Related Art

Various different forms of apparatuses heretofore have been provided for introducing deodorizing chemicals into the air passages of air conditioning systems and providing a deodorant to the interior of a motor vehicle while the vehicle air conditioning system is in operation. Examples of these previously known apparatuses are disclosed in U.S. Pat. Nos. 2,683,074, 2,874,032, 3,044,276, 3,049,399, 3,269,602, 3,420,445, 3,633,881, 4,028,073, 4,303,617, 4,309,382 and 4,563,333. However, these previously known devices do not include the overall combination of structural and operational features of the instant invention.

SUMMARY OF THE INVENTION

Most vehicle air conditioning systems include air handling duct structure having inlet and outlet ends, a squirrel cage blower serially disposed in the duct structure closely adjacent the inlet end thereof, heater and air conditioner heat exchangers serially connected in selectively and jointly usable intermediate length sections of the duct structure and conditioned air outlets (of varied types) comprising the outlet end of the air handling duct structure.

Inasmuch as a deodorizer liquid (with or without a disinfectant added thereto) is capable of excessively wetting the blade portions of the rotor of a squirrel cage blower and cause excessive dirt buildup thereon when the blower is operated in dusty environments, it is not desirable to spray inject or otherwise introduce a liquid deodorant into the air handling duct structure of a vehicle heating and air conditioning system upstream from the squirrel cage blower thereof. However, it is important for efficient operation of a deodorizing liquid (especially if having a disinfectant added thereto) introduced into an air handling duct structure of the type used in automobile air conditioning systems for the point of introduction of the liquid deodorant into the duct system to be closely adjacent but on the downstream side of the blower and upstream from the heat exchangers.

Accordingly, a need exists for structure by which a liquid deodorant (possibly including a disinfectant) may be introduced into the air handling duct structure of an automotive heating and air conditioning system immediately downstream from the blower thereof and upstream from the heat exchangers.

The main object of this invention is to provide a simplified apparatus for introducing a deodorant liquid (which may include a disinfectant) into a vehicle heating and air conditioning air handling duct system immediately downstream from the blower section thereof and upstream from the heat exchangers.

Another object of this invention is to provide a deodorant injection system which may be readily incorporated into the manufacture of new automobiles.

Yet another object of this invention is to provide a deodorant injection system in accordance with the preceding objects and which may be readily added to existing automotive air conditioning systems with only the use of simple tools and by persons having only minimal mechanical ability.

A further object of this invention is to provide a deodorant injection system for a vehicle heating and air conditioning system and which may be automatically actuated or manually actuated, as desired.

Still another object of this invention is to provide a deodorant injection system for any general air handling duct structure.

A final object of this invention to be specifically enumerated herein is to provide a deodorant injection system in accordance with the preceding objects and which will conform to conventional forms of manufacture, be of simple construction and easy to install so as to provide a device that will be economically feasible, long lasting and relatively trouble free in installation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
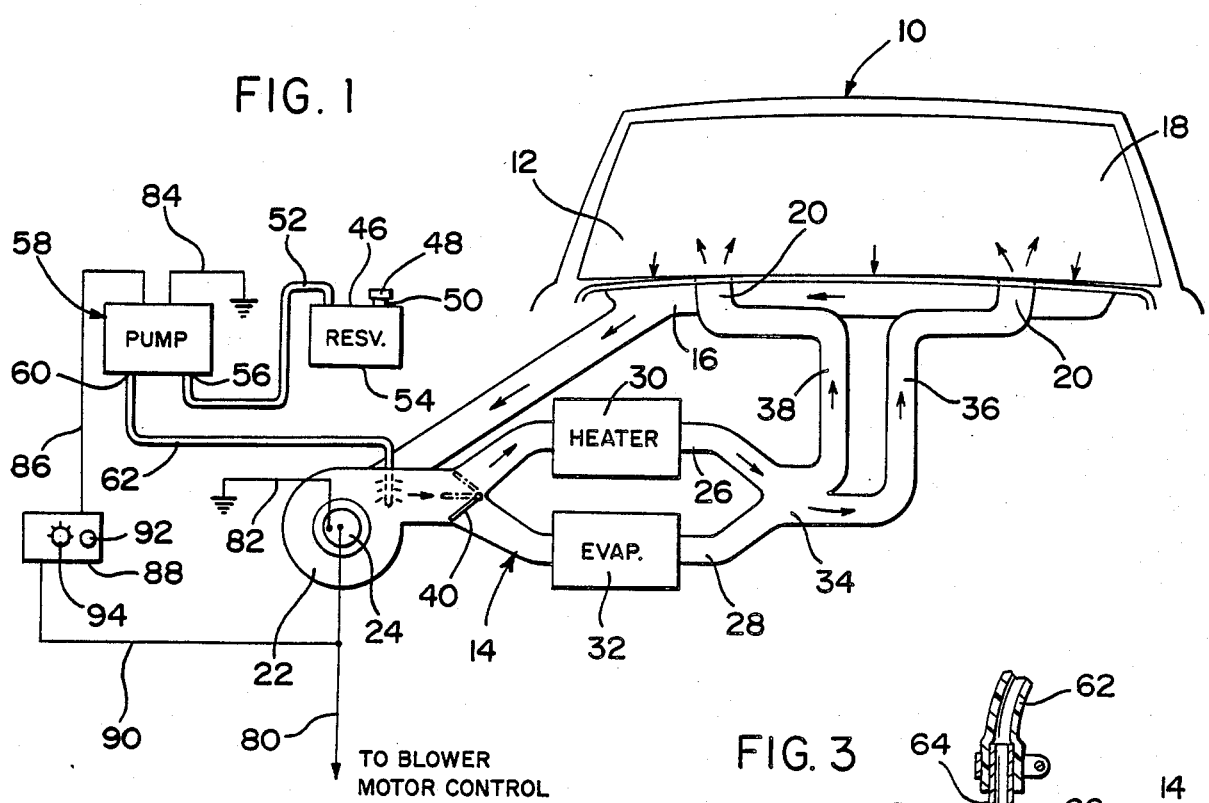
FIG. 1 is a schematic view of a typical automotive heating and air conditioning system and illustrating the deodorizing injection system of the instant invention operatively associated therewith.

Referring now more specifically to the drawings, the numeral 10 generally designates a fragmentarily illustrated conventional form of automotive vehicle including an interior passenger compartment 12. The vehicle 10 further includes air handling duct structure referred to in general by the reference numeral 14 incorporating an inlet end 16 opening outwardly immediately forward of the lower marginal portion of the windshield 18 of the vehicle 10 and an outlet end incorporating duct outlets 20 opening into the vehicle interior 12 behind the windshield 18. The duct outlets 20 may of course be in the form of defroster outlets, dashboard outlets and/or under dash outlets (only the defroster outlets 20 being illustrated for simplicity reasons).

Serially connected in the duct structure 14 closely adjacent the inlet end 16 is a squirrel cage blower assembly 22 powered by an electric motor 24 and closely downstream of the blower assembly the duct structure 14 branches into a pair of duct sections 26 and 28 having a heater core 30 and an evaporator coil 32, respectively, serially connected therein. The downstream ends of the duct sections 26 and 28 open into each other as at 34 and then branch into separate defroster ducts 36 and 38 whose outlet ends define the duct outlets 20. In addition, an airflow diverter valve 40 is disposed in the duct structure 28 downstream from the blower assembly 22 and at the point the duct structure branches into the inlet ends of the duct sections 26 and 28, whereby air discharged from the blower assembly 22 may be completely diverted to either the duct section 26 or the duct section 28, or be adjustably discharged into both duct sections 26 and 28.

It is to be noted that the ducting arrangement of the air handling duct structure of automobiles of different manufacture vary to some degree, but the air handling duct structure 14 is to be considered as exemplary of a typical air handling duct structure of an automotive type vehicle.

Conventionally, the duct structure 14 is constructed of plastic and/or fiberglass and includes a fully exposed upper wall 42 within the rear of the engine compartment of the vehicle 10 immediately forward of the fire wall (not shown) thereof.

The deodorizer injection system of the instant invention includes a liquid reservoir 46 which may be filled by removing a removable closure 48 of a filler neck 50 and an outlet tube 52 extends from the interior of the reservoir 46 closely above the bottom 54 thereof to the inlet 56 of an electric motor and pump assembly referred to in general by the reference numeral 58. The assembly 58 includes an outlet 60 from which a discharge tube 62 extends and the outlet end of the discharge tube 62 is removably telescoped and clamped over the inlet end 64 of an injection tube 66. The outlet end 68 of the injection tube 66 includes a plurality of radial outlet bores 70 formed therein and the terminal end of the outlet end 68 has a spray jet discharge nozzle 72 mounted thereon.

Figure 3:
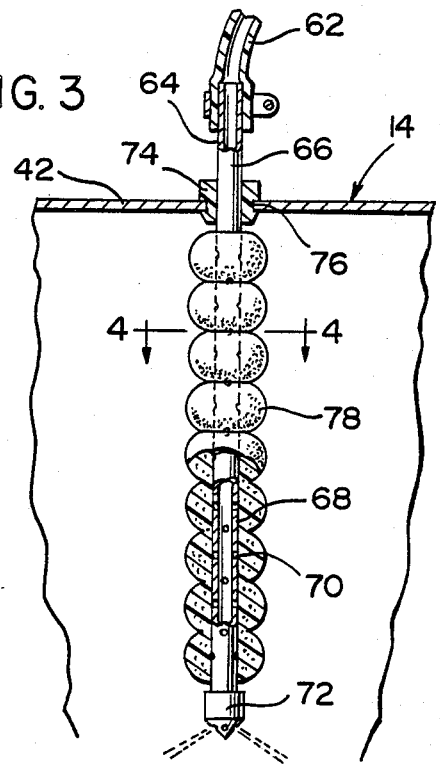
FIG. 3 is an enlarged fragmentary vertical sectional view taken substantially upon the plane indicated by the section line 3—3 of FIG. 2.
Figure 2:
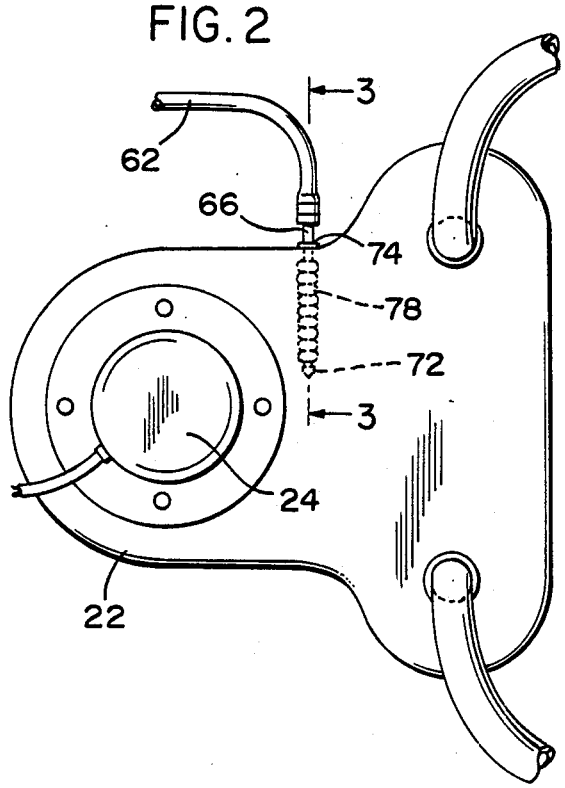
FIG. 2 is an enlarged elevational view of a typical squirrel cage blower mounting location on the air handling duct structure portion of a typical automotive air conditioning and heating system projecting forward of the fire wall of the vehicle and into the engine compartment thereof.
Figure 4:
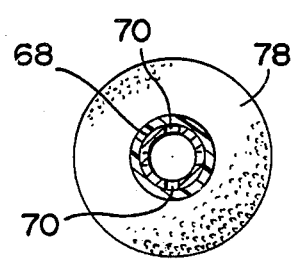
FIG. 4 is an enlarged horizontal sectional view taken substantially upon the plane indicated by the section line 4—4 of FIG. 3.

The injection tube 66 is tightly received through a grommet 74 mounted in an opening 76 provided therefor in the upper wall 42 and the injection tube 66 is thus frictionally mounted in the position thereof illustrated in FIG. 3. In addition, the outlet end 68 of the injection tube 66 disposed below the upper wall 42 includes a wrap of liquid absorbent foam material 78. The discharge nozzle 72 is of a diameter to be received through the opening 76 and the wrap of foam material 78 may be forced through the opening 76 from thereabove as the outlet end 68 of the injection tube 66 is downwardly inserted through the opening 76. Of course, the opening 76 and grommet 74 may be increased in diameter, if desired. Furthermore, other means may be used for supporting the injection tube 66 from the upper wall 42 and sealing the upper wall 42 about the injection tube 66.

The motor 24 receives current through a conductor 80 from the blower motor control (now shown) of the vehicle 10 and is grounded through a conductor 82. The motor of the assembly 58 is grounded by a conductor 84 and receives current through a conductor 86 from a control 88, the control 88 receiving current through a conductor 90 from the conductor 80, the control 88 and the motor 24 thus being connected in parallel to the electrical system of the vehicle 10. The control 88 is of the type including a momentary on/off button switch 92 for momentarily bridging the conductors 86 and 90 as well as a timer control switch 94 (including an off position). If the duct system 14 is to have a deodorant (and possibly a disinfectant) injected thereinto at the control of the operator of the vehicle 10, the switch 94 may be turned to the off position and the switch 92 may be momentarily actuated as desired by the vehicle driver, the control 88 being disposed within the interior 12 of the vehicle 10 for ready access by the vehicle driver. Inasmuch as the conductor 90 is connected in paralle to the blower motor control, the motor of the assembly 58 may be actuated only when the blower motor 24 is operative.

If operation of the motor of the assembly 58 and thus injection of deodorant into the duct system 14 is to be automatically controlled, the time control switch 94 may be adjusted so that operation of the motor of the assembly 58 will occur only for a preset time interval each time the blower motor control actuates the electric motor 24.

Upon actuation of the motor of the assembly 58, liquid deodorant (and any disinfectant therein) is pumped from the reservoir 46, through the assembly 58 and into the injection tube 66. A portion of the liquid is discharged from the nozzle 72 and the remaining portion of the pumped liquid is absorbed by the wrap of foam material 78 for subsequent evaporation therefrom into the air passing through the duct structure 14. It will be noted that operation of the motor of the assembly 58 will occur for only relatively short periods of time, in most instances.

If it is desired, the wrap of foam material 78 may be omitted as well as the bores 70 or, alternately, the discharge nozzle 72 may be omitted and the terminal end of the outlet end 68 of the tube 66 may be plugged. However, for most efficient operation whenever a deodorant injection is desired, both the discharge nozzle 72 and wrap of foam material 78 will be used.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

We claim:

1. In combination an automotive vehicle including an engine compartment, an air handling duct structure incorporating inlet and outlet ends and heat exchange means serially disposed within said duct structure intermediate said ends as well as blower means serially disposed in said duct structure at a location therealong intermediate said inlet end and said heat exchange means, a liquid injection system for said duct structure, said duct structure including an exposed upper wall portion thereof within said engine compartment and in part defining said duct structure location and to which ready access may be had from the exterior of said duct structure, an elongated liquid injection tube having inlet and outlet ends, said exposed wall portion having an opening formed therethrough, said outlet end of said injection tube being projected downwardly through said opening into the interior of said duct structure at said location, means sealing said tube relative to said exposed upper wall portion about said opening, said outlet end of said tube being generally vertically disposed and spaced below said upper wall portion, said outlet end including liquid discharge means for discharging liquid supplied to said inlet end from said outlet end of said tube to the exterior thereof, and liquid under pressure supply means for supplying a deodorizer liquid under pressure to said inlet end, said supply means including actuator means therefor operative to momentarily actuate said supply means, said liquid discharge means including radial openings formed in said outlet end of said tube, said outlet end of said tube including a liquid absorbent wrap disposed thereover and projectable downwardly through said opening with said outlet end of said tube, said wrap being operable to absorb liquid discharged from said radial bores and to enable the absorbed liquid to be evaporated therefrom.

2. The combination of claim 1 wherein said actuator means also includes means for timer actuation of said supply means.

3. The combination of claim 1 wherein said blower means includes an electrically powered blower motor, said actuator means including an electrically powered operator, said electrically powered operator being operative only when electrical power is supplied to said blower motor.

4. The combination of claim 1 wherein said liquid discharge means includes a spray discharge nozzle on the lower terminal end of said outlet end of said tube.

* * * * *